United States Patent
Kalogiros et al.

(10) Patent No.: US 10,265,580 B2
(45) Date of Patent: Apr. 23, 2019

(54) BICYCLE TRAINER (71) Applicant: SBI Media Holding SA, Delemont, Jura (CH)

(72) Inventors: James Kalogiros, Jura (CH); Fadi Yassmin, Jura (CH); Peter Berlowitz, Jura (CH)

(73) Assignee: SBI Media Holding SA, Jura (CH)

( * ) Notice: Subject to any disclaimer, the term of this patent is extended or adjusted under 35 U.S.C. 154(b) by 0 days.

(21) Appl. No.: 15/025,477

(22) PCT Filed: Sep. 27, 2013

(86) PCT No.: PCT/EP2013/070221
§ 371 (c)(1),
(2) Date: Mar. 28, 2016

(87) PCT Pub. No.: WO2015/043658
PCT Pub. Date: Apr. 2, 2015

(65) Prior Publication Data
US 2016/0236036 A1    Aug. 18, 2016

(51) Int. Cl.
*A61B 5/024* (2006.01)
*A63B 21/00* (2006.01)
(Continued)

(52) U.S. Cl.
CPC .......... *A63B 24/0075* (2013.01); *A61B 5/024* (2013.01); *A63B 21/0058* (2013.01); *A63B 21/00178* (2013.01); *A63B 22/0023* (2013.01); *A63B 23/0476* (2013.01); *A63B 24/0062* (2013.01); *A63B 24/0087* (2013.01); *A63B 69/16* (2013.01); *A63B 71/0619* (2013.01); *A63B 21/00196* (2013.01); *A63B 21/023* (2013.01); *A63B 24/0084* (2013.01); *A63B 2022/0641* (2013.01); *A63B 2024/0009* (2013.01); *A63B 2024/009* (2013.01); *A63B 2024/0012* (2013.01); *A63B 2024/0068* (2013.01); *A63B 2069/163* (2013.01); *A63B 2069/164* (2013.01); *A63B 2069/166* (2013.01); *A63B 2069/167* (2013.01);
(Continued)

(58) Field of Classification Search
CPC ...... A63B 22/06–2022/0658; A63B 2024/009; A63B 69/16–2069/168; A63B 24/0084
See application file for complete search history.

(56) References Cited

U.S. PATENT DOCUMENTS 4,976,424 A * 12/1990 Sargeant ............ A63B 21/0053
482/3
5,364,271 A * 11/1994 Aknin .............. A63B 21/00181
273/148 B
(Continued)

FOREIGN PATENT DOCUMENTS

DE    32 18 086    12/1983
DE    34 04 539    8/1985
(Continued)

*Primary Examiner* — Jennifer M Deichl
(74) *Attorney, Agent, or Firm* — Norris McLaughlin, P.A.

(57) ABSTRACT

A bicycle trainer for mounting a bicycle includes a roller for engaging the rear wheel of the bicycle, and a motor controlled by an electrouros unit and providing driving and braking forces to the roller. The bicycle trainer is used in a method for comparative home training.

28 Claims, 8 Drawing Sheets (51) Int. Cl.
*A63B 21/02* (2006.01)
*A63B 22/00* (2006.01)
*A63B 22/06* (2006.01)
*A63B 23/04* (2006.01)
*A63B 24/00* (2006.01)
*A63B 69/16* (2006.01)
*A63B 71/00* (2006.01)
*A63B 71/02* (2006.01)
*A63B 71/06* (2006.01)
*A63B 21/005* (2006.01)

(52) U.S. Cl.
CPC . *A63B 2069/168* (2013.01); *A63B 2071/0072* (2013.01); *A63B 2071/025* (2013.01); *A63B 2071/0638* (2013.01); *A63B 2220/51* (2013.01); *A63B 2220/54* (2013.01); *A63B 2220/72* (2013.01); *A63B 2220/75* (2013.01); *A63B 2220/76* (2013.01); *A63B 2220/78* (2013.01); *A63B 2225/09* (2013.01); *A63B 2225/20* (2013.01); *A63B 2230/015* (2013.01); *A63B 2230/062* (2013.01)

(56) References Cited

U.S. PATENT DOCUMENTS

| | | | |
|---|---|---|---|
| 6,857,992 B1* | 2/2005 | Kolda | A63B 21/0051 |
| | | | 482/61 |
| 2010/0004097 A1* | 1/2010 | D'Eredita | A63B 24/0062 |
| | | | 482/8 |
| 2012/0238412 A1* | 9/2012 | Hamilton | A63B 24/0087 |
| | | | 482/61 |

FOREIGN PATENT DOCUMENTS

| | | |
|---|---|---|
| FR | 2 755 866 | 5/1998 |
| WO | WO-96/19264 | 6/1996 |
| WO | WO-96/36399 | 11/1996 |

* cited by examiner

BICYCLE TRAINER

BACKGROUND OF THE INVENTION

The present invention relates to an improved bicycle trainer.

Several different kinds of bicycle trainers are known in the prior art. On the one hand, there are so-called stationary bicycles or exercise bicycles which resemble a bicycle without true wheels. Such stationary bicycles are used for indoor cycling or spinning. Typically, these stationary bicycles provide certain pre-programmed artificial profiles which are supposed to simulate, e.g., different slopes such as downhill cycling or uphill cycling by adjusting the resistance accordingly. However, cycling on such a stationary bicycle, while being advantageous for training purposes, can by no means be compared to real cycling on a road. Moreover, professional or semi-professional cyclists typically like using their own bicycle for training purposes. Thus, there are two different kinds of bicycle trainers which may be used in combination with a real bike. A first type of trainer (also called turbo trainer) is a piece of equipment that makes it possible to ride a bicycle while it remains stationary. Such a trainer typically comprises a frame, a clamp to hold the bicycle securely, a roller that presses up against the rear wheel of the bicycle, and a mechanism that provides resistance when the pedals are turned. These trainers are categorized by how the unit provides resistance into wind trainers, magnetic trainers, fluid trainers, centrifugal trainers and utilitarian trainers. In all these trainers of the first type, the bicycle is fixedly mounted onto the trainer and remains entirely stationary during training. Typically, the trainer is fixedly mounted to the rear axle of the bicycle. An entirely different, second type of bicycle trainers are the so-called bicycle rollers which, unlike other types of bicycle trainers, do not attach to the bicycle frame. These bicycle rollers normally comprise three cylinders, drums or rollers, two for the rear wheel and one for the front wheel, on top of which the bicycle rides. A belt may connect one of the rear rollers to the front roller causing the front wheel of the bicycle to spin when the bicycle is pedaled. The rider must balance him- or herself on the rollers while training.

SUMMARY OF THE INVENTION

However, none of these known bicycle trainers is able to provide an experience which is adequately similar to riding a real bicycle on the road. It is thus an object of the present invention to provide a bicycle trainer which simulates the conditions of cycling on the road as closely as possible. It is a further object of the present invention to provide a method for comparative home training which allows for cycling on a real track at home.

The present invention relates to a bicycle trainer for mounting a bicycle having a frame and a rear wheel attached to a rear axle. The bicycle trainer comprises a roller for engaging with the rear wheel of the bicycle, the roller being adapted to transmit a driving force and a braking force to the rear wheel, a motor adapted to actively provide the driving and braking forces to the roller, and an electronics unit for controlling the motor. When the bicycle is mounted to the trainer, the bicycle is, at least in part, supported by the roller. Preferably, the electronics unit is adapted to simulate driving and braking forces of a predetermined track within a predetermined terrain. Of course, the driving and braking forces transmitted to the rear wheel correspond to driving and braking moments. Even though reference is made throughout this invention to forces the skilled person will be readily able to switch to moments instead as the lever arm is known.

While bicycle trainers known in the prior art typically just have a mechanism that provides resistance when the pedals are turned which resistance, in the case of some known bicycle trainers, may be adjusted, providing resistance is by far not sufficient to simulate a real cycling situation. For example, if the simulated track comprises a downhill passage, the rear wheel should—under real life conditions—continue spinning even if the user stops pedaling. This can, however, not be achieved by simply adjusting resistance. By contrast, the motor of the bicycle trainer of the present invention is adapted to actively provide driving forces to the roller which allows for maintaining the angular velocity of the rear wheel or even accelerating the rear wheel without any force being provided by the user. Similarly, actively providing driving forces to the roller by means of a motor also allows for simulating inertia, e.g., on a straight track. Thus, the bicycle trainer of the present invention provides a real life road feeling as the entire force or torque transmission from the pedals over the hub at the rear axle to the roller is quite similar to that from the pedals to a road during real life conditions. Due to the direct weight bearing on the roller, the same power output as on the road may be generated because said design effectively avoids any slippage of the tire on the roller.

According to the present invention, the predetermined track within a predetermined terrain is not an artificial bogus track as is the case with known trainers, but rather may correspond to a track existing in the real world. For example, the predetermined track may correspond to a stage of a bicycle race such as the Tour de France or to a track previously followed by the user with his bicycle in the real world. Preferably, data of such a predetermined track within a predetermined terrain such as the slope and rolling resistance along the track have been saved previously, e.g., by the user, and uploaded to the electronics unit of the bicycle trainer. The user may then choose a predetermined track out of several saved predetermined tracks and have a virtual reality experience of riding said very track with his own bike. In other words, the forces needed for pedaling are adjusted to all the saved track data such as the slope of the track and the rolling resistance along the track.

Preferably, the electronics unit is adapted to simulate driving and braking forces under predetermined environmental conditions. These predetermined environmental conditions may comprise one or a combination of wind, rain, humidity, temperature and inertia. If, for example, the actual wind, which was present during a specific stage of a cycling race such as the Tour de France was, measured and saved for the entire track profile, the electronics unit may take the reduced or increased air resistance into account and, accordingly, adapt the driving and braking forces on the basis of these data. Similarly, rain and/or humidity may change the rolling resistance and an increased temperature may, e.g., be simulated by increasing the resistance to the roller. It is preferred that the user may change these environmental conditions upon request and, e.g., compare the virtual reality experience of a given track with real wind conditions with the same track without wind.

Preferably, the driving and braking forces are simulated taking the weight of a user into account. According to one preferred embodiment, the user may input his weight into the electronics unit via a keyboard or a touch display. According to another preferred embodiment, the bicycle trainer may comprise a balance in order to actually measure the weight of the user once sitting on the mounted bicycle.

The weight of the user is preferably taken into account by calculating effects of inertia and/or increased resistance along an uphill track. Of course, the power needed for cycling uphill in real life depends on the weight of the cyclist, which may be perfectly simulated by calculating the downward force on the user due to the earth's gravity on the basis of the user's weight taking the known slope into account. In an analogous manner the power needed for cycling downhill is accordingly reduced due to the gravitational force. Similarly, the inertia of a rolling bicycle depends on the weight of the user.

It is preferred that the electronics unit is adapted to measure the force and/or torque transmitted from the rear wheel to the roller. Preferably, the driving and braking forces and/or torques provided to the roller are adjusted in response to the measured force and/or torque. Preferably, the force and/or torque transmitted from the rear wheel to the roller is measured at least once within each pedal stroke. Preferably, the motor is adapted to adjust the force and/or torque provided to the roller within less than 50 ms, more preferably within less than 25 ms and even more preferably within less than 10 ms. In other words, the motor is adapted to immediately adjust the driving and braking forces and/or or torques to the roller if the user, e.g., reduces his pedaling force.

Preferably, one and the same motor is used for providing a driving torque and for providing a braking torque, i.e. for actively providing resistance. A controller repeatedly calculates whether to resist the user's pedaling strokes or to actively drive the roller in order to account for, e.g., effects of inertia. For this purpose, preferably both the speed of the roller and the motor current are repeatedly or constantly measured. Preferably, pulse width modulation is used in order to control the motor. Then, the current may be measured, e.g., with an analog to digital converter.

On the basis of the actual speed of the roller and the measured motor current the controller may calculate whether the motor has to provide resistance or support based on the actual track position (slope etc.) and environmental conditions (wind etc.). Accordingly, the motor will provide an accelerating or decelerating force or torque to the roller. In other words, on the basis of the measured power input by the user the controller may calculate a roller speed which would be caused by said power input under real life conditions. The motor is then controlled to assist or resist in order to achieve this calculated target speed using pulse width modulation.

Preferably, the electronics unit is adapted to provide data for displaying terrain data and/or environmental conditions. For example, the real view a cyclist would have along the track may be simulated and/or displayed by capturing image data with, e.g., a camera mounted on the bicycle following the track in the real world. These image data may be comprised in a predetermined terrain data set and saved on or uploaded to the electronics unit. If a display (e.g., a TV screen or a laptop) is connected to the bicycle trainer, the electronics unit may provide these image data or other terrain data and/or environmental conditions to the display for displaying it to the user. Thus, the user when riding on the bicycle trainer may see the real terrain of the predetermined track as a video on the display. This further improves the quality of the virtual reality experience and may provide additional motivation to the user because he may, indeed, see on the display that he is riding uphill while being forced to provide more power. In addition or alternatively, terrain data and/or environmental conditions may simply be displayed in pictograms and/or by means of numbers. For example, the display may show the speed of the bicycle, the slope of the current track, wind data and the like.

It is preferred that the electronics unit is further adapted to save and/or upload track data of a user and/or professional and to provide comparative data for displaying which allow for a direct comparison of the current performance of a user with the saved and/or uploaded track data. For example, the user may choose to save and/or upload track data of a specific professional who has taken part in a specific bicycle race. The user may then choose the corresponding track and follow said very track on the bicycle trainer in a virtual reality experience. He may then be provided with information how fast the specific professional was along the track, and/or how quickly the professional was pedaling. In addition or alternatively, the user may be provided with physiological data of the specific professional such as his heart rate along the track. In this manner, the user may actually take part in a bicycle race in virtual reality and may much better appreciate the performance of a specific professional. Alternatively, the user may upload track data of his own which were saved when the user was following the track in the real world. He may thus compare his at-home performance with the previous real life performance. Alternatively, a user or professional may use such track data to prepare for a race in real life.

It is further preferred that the electronics unit is adapted to receive a live track data stream, preferably via the internet, and to provide comparative data for displaying which allow for a direct comparison of the current performance of a user with a simultaneous performance evaluated from the live track data stream. Thus, the user may even simultaneously take part in a bicycle race.

Preferably, at least 10%, more preferably at least 25% and even more preferably at least 40% of the weight of the bicycle (and the user) is supported by the roller, when the bicycle is mounted to the trainer. In other words, it is preferred that the rear wheel rests or sits on the roller and that the weight resting on the rear axle is completely carried by the roller.

It is further preferred that the trainer comprises two rollers for engaging with the rear wheel of the bicycle, one of the two rollers being adapted to transmit the driving force and the braking force to the rear wheel. In this case, the entire weight resting on the rear axle is preferably carried by these two rollers.

Preferably, the bicycle trainer further comprises means for mounting a front wheel of the bicycle, wherein the slope of a line connecting the roller to the means for mounting a front wheel can be adjusted. In other words, the bicycle can preferably be rotated around an axis perpendicular to the longitudinal axis of the bicycle and parallel to the axis of the rear axle. Thus, the virtual reality experience can even be further improved because cycling, e.g., uphill, in this embodiment not only changes the resistance of the roller but also adjusts the way the user is positioned on the bicycle in accordance with the slope of the track. Preferably, the bicycle trainer further comprises a platform on top of which the bicycle trainer is placed, wherein the slope can be adjusted by tilting the entire platform. Preferably, tilting the platform is achieved by an additional motor which is preferably controlled by the electronics unit. Preferably, the electronics unit is adapted to not only simulate driving and braking forces of a predetermined track within a predetermined terrain, but also to simulate the slope of the predetermined track by, e.g., tilting the platform. It is also preferred that the bicycle trainer further comprises a motor adapted to vibrate the platform. Preferably, the frequency spectrum of the applied vibration corresponds to typical vibrations measured along the predetermined track.

The bicycle trainer described above corresponds to a first aspect of the present invention. In the following, a bicycle trainer according to a second aspect of the present invention is described. The second aspect, inter alia, focuses on the possibility to allow for a tilting movement of the bicycle out of the vertical. It is to be emphasized that each and every feature of the bicycle trainer according to the first aspect of the present invention may be combined with each and every feature of the bicycle trainer according to the second aspect of the present invention. In particular, every feature of the first aspect of the present invention aiming at the virtual reality experience may also be applied for the bicycle trainer according to the second aspect.

In this second aspect the present invention relates to a bicycle trainer comprising a support for supporting a bicycle having a frame and a rear wheel attached to a rear axle. The support comprises means for biasing the bicycle into an upright orientation. The bicycle trainer further comprises a roller for engaging with the rear wheel of the bicycle. When the bicycle is supported by the support, the roller is adapted to provide resistance against turning the rear wheel. The rear axle of the bicycle is not directly connected or mounted to the support of the bicycle trainer. In other words, the rear axle and the rear wheel of the bicycle are, to a certain extent, free to move. Preferably, the rear wheel of the bicycle is free to move in a lateral direction on the roller when the bicycle is supported by the support. In addition or alternatively, the support preferably allows for lifting the rear wheel off the roller, when the bicycle is supported by the support.

Mounting the bicycle frame with a portion other than the rear axle to the support of the bicycle trainer substantially improves the natural feeling provided during training on the inventive bicycle trainer. Simulating a real life situation is on the one hand substantially improved by allowing lateral and/or vertical movement of the rear axle/rear wheel. On the other hand, transmitting any biasing force that resists tilting of the frame via the rear axle feels unnatural, because the force is introduced at the rear end of the bicycle frame, whereas during cycling on the road these biasing forces are provided by inertia and/or torques created by pedaling. These forces are typically introduced into the bicycle frame at a rather central portion of the frame. It is therefore particularly preferred to mount the bicycle frame to the support at a position of the bicycle frame between the front axle and the rear axle, preferably in a central region between the front axle and the rear axle. According to a preferred embodiment, the support of the bicycle trainer supports the bicycle at the down tube of the bicycle frame.

Preferably, the bicycle is supported by the support in such a manner that, during use, at least 80%, preferably at least 90% and more preferably at least 95% of the weight of the bicycle (and the user) is carried by the front wheel and the rear wheel. This should at least be the case as long as the bicycle is oriented in an upright orientation. If the bicycle is tilted, the means of biasing the bicycle into an upright orientation evidently also carries a small portion of the weight. Preferably, the rear wheel of the bicycle is supported by the roller, when the bicycle is mounted to the support. In other words, it is preferred that the rear wheel rests or sits on the roller and that the weight resting on the rear axle is completely carried by the roller. If two rollers are provided for the rear wheel, the entire weight resting on the rear axle is carried by these two rollers. This is particularly advantageous, because the rider gets the impression of really riding on a road as the entire force transmission from the pedals to the roller is quite similar to that from the pedals to a road. Moreover, due to the direct weight bearing on the one or two rollers the same power output as on the road may be generated because said design effectively avoids any slippage of the tire on the roller.

The means for biasing is preferably adapted to allow for a tilting movement of the bicycle. Preferably, the means for biasing is adapted to provide a torque biasing the bicycle into an upright orientation of the bicycle beyond a predetermined first critical angle versus the vertical. The first critical angle is preferably smaller than 1°, more preferably smaller than 0.5° and most preferably about 0°. According to a first preferred embodiment, no biasing torque is provided up to said first critical angle, whereas at and beyond said critical angle the biasing means provides a torque biasing the bicycle into an upright orientation. According to a second preferred embodiment (corresponding to the first critical angle being about 0°), the means for biasing always provides a torque biasing the bicycle into an upright orientation.

It is further preferred that the bicycle trainer comprises a stop adapted to avoid a tilting movement of the bicycle beyond a predetermined second critical angle versus the vertical. The second critical angle preferably lies in a range between 2° and 6°, more preferably between 3° and 5° and most preferably is about 4°. In a particularly preferred embodiment, a constant force or torque biasing the bicycle into an upright orientation is provided over the entire from −4° to +4°.

Preferably, the means for biasing is adapted to be, directly or indirectly, connected to the bicycle frame at a portion other than the rear axle, more preferably to the down tube of the bicycle frame. The connection of the bicycle frame to the biasing means is preferably releasable and can preferably be adapted to different types and sizes of bicycles.

The means for biasing preferably further comprises two independent springs. The springs are preferably adapted to provide a torque biasing the bicycle into an upright orientation. The amount of the torque can preferably be adjusted by means of a motor. Alternatively, it may also be possible to adjust the torque manually. It is preferred that the torque can be adjusted by changing the lever arm acting on the springs. Preferably, the torque can be adjusted in a range between about 5 Nm and about 200 Nm, more preferably between about 15 Nm and about 150 Nm and even more preferably between about 25 Nm and about 100 Nm. Alternatively, it may be possible to adjust the spring force of the springs.

The bicycle trainer preferably further comprises a motor adapted to adjust the resistance against turning the rear wheel. The resistance is preferably actively provided by the motor itself. Preferably, the motor is provided within the roller. It is further preferred that the motor is also adapted to actively provide a driving force to the rear wheel.

Preferably, two rollers are provided for the rear wheel wherein one roller is adapted to actively transmit a driving force and/or a braking force to the rear wheel, whereas the second roller may rotate without providing any substantial resistance. Providing two rollers further improves the "real road feeling" as the tire is better supported on two rollers than with a single contact point (of two convex curves).

Preferably, the support for supporting the bicycle comprises a front portion for mounting the front wheel of the bicycle. Preferably, the front wheel is mounted stationary, i.e., the front wheel cannot be turned. The distance between the mounting for the front wheel and the roller(s) for the rear wheel can preferably be adjusted in order to adapt the bicycle trainer to different types and sizes of bicycles. Moreover, the mounting for the front wheel can preferably be adjusted to wheels/tires having different widths.

The means for biasing the bicycle into an upright orientation preferably comprises a system of posts or rods for attaching to the down tube of the bicycle. Preferably, said system comprises a cylinder and a piston or inner sleeve which can move up and down within said cylinder. This allows for mounting the bicycle to the support without transmitting any substantial force along the vertical direction. In other words, the bicycle, once mounted, may be moved up and down by simply overcoming the resistance between piston and cylinder. The system of rods or posts preferably further comprises an additional rod being pivotably attached to the piston. This allows adjustment for different orientations of the down tube of different types and sizes of bikes.

The bicycle trainer preferably further comprises an additional motor for adjusting the lever arm of the means for biasing the bicycle into an upright orientation. Preferably, changing the lever arm does not change the extension or compression of the springs, but only changes the lever arm acting on the springs. Preferably, tilting the bicycle in one direction only compresses one of the two springs, but does not extend the other of the two springs.

The above description relates to two aspects of a bicycle trainer according to the present invention. In the following, a method for comparative home training will be described. Said method according to the present invention may be utilized with a bicycle trainer according to either of the two aspects described above.

According to a third aspect, the present invention relates to a method for comparative home training. Accordingly, a bicycle trainer comprising a roller, an electronics unit and a motor adapted to actively provide driving and braking forces to the roller, is provided. A bicycle having a frame and a rear wheel is mounted onto the bicycle trainer such that the roller engages with the rear wheel of the bicycle. Furthermore, a display is provided, wherein said display may be part of the bicycle trainer or a separate display such as a TV-screen or a laptop display. Data of a predetermined track are uploaded onto the electronics unit. Then, a predetermined track is simulated by actively providing driving and braking forces to the roller and by displaying at least some of the data while a user is cycling on the bicycle.

Preferably, the data comprises terrain data, wherein the predetermined terrain comprises one or a combination of slope and rolling resistance. Preferably, the data further comprises environmental conditions such as wind, rain, humidity, temperature and rider's inertia. Preferably, the data further comprises image data taken along the predetermined track.

Thus, simulating the predetermined track by displaying at least some of the data while a user is cycling on the bicycle may comprise displaying image data, i.e., a video, taken previously along the predetermined track and/or displaying, by means of a pictogram or in terms of numbers, the current slope of the track and the actual rolling resistance and/or the environmental conditions such as wind, rain, humidity, temperature and rider's inertia.

Simulating the predetermined track preferably further comprises calculating the driving and braking forces on the basis of one or a combination of slope, rolling resistance, wind, rain, humidity, temperature, inertia, weight of the user.

The method according to the present invention preferably further comprises the step of measuring the force transmitted from the rear wheel to the roller while the user is pedaling.

It is preferred that the driving and braking forces provided to the roller are adjusted in response to the measured force.

Preferably, track data of a user and/or professional are saved and/or uploaded and comparative data are displayed, which allow for a direct comparison of the current performance of the user with the saved and/or uploaded track data. The uploaded track data may preferably be uploaded as a live track data stream which is preferably uploaded via the internet. Said track data preferably comprise one or a combination of the following data: velocity, revolution speed or cadence, physiological data such as heart rate. The method preferably further comprises measuring and/or calculating one or a combination of the following data of the user's performance: velocity, revolution speed, physiological data such as heart rate. While velocity may be calculated by measuring the velocity of the roller, measuring and/or calculating revolution speed and/or physiological data may require additional sensors or measuring devices. For example, revolution speed may be measured by an inductive, a camera or a photo sensor. Physiological data such as heart rate may be measured by providing the user with a respective sensor carried on the body. The sensor is preferably adapted to communicate, either by an electric connection or wirelessly, with the electronics unit of the bicycle trainer.

The bicycle trainer of the present invention as well as the method for comparative home training of the present invention are superior over known trainers and methods of the prior art because they allow for an excellent virtual reality experience which combines a hardware (i.e., bicycle trainer plus bike) which almost exactly simulates real life conditions with displaying a corresponding virtual reality on a display. This not only allows for perfectly simulating real life conditions, but also enables a user to directly and even simultaneously compete with a professional.

Further advantages of the present invention will be evident from the detailed description of the preferred embodiments with reference to the following Figures, which show.

BRIEF DESCRIPTION OF THE DRAWINGS

DETAILED DESCRIPTION OF THE INVENTION

FIGS. 1-8 show a preferred embodiment of a bicycle trainer according to the second aspect of the present invention. While the preferred embodiment shows a specific bicycle trainer which also allows for a tilting movement of the bicycle out of the vertical, it is to be emphasized that the present invention, in particular aspects 1 and 3 of the present invention, are not limited to embodiments allowing for such a tilting movement. However, the features described in the following with respect to FIGS. 1-8 may be advantageously combined with all features of the first and third aspect of the present invention.

Figure 1:
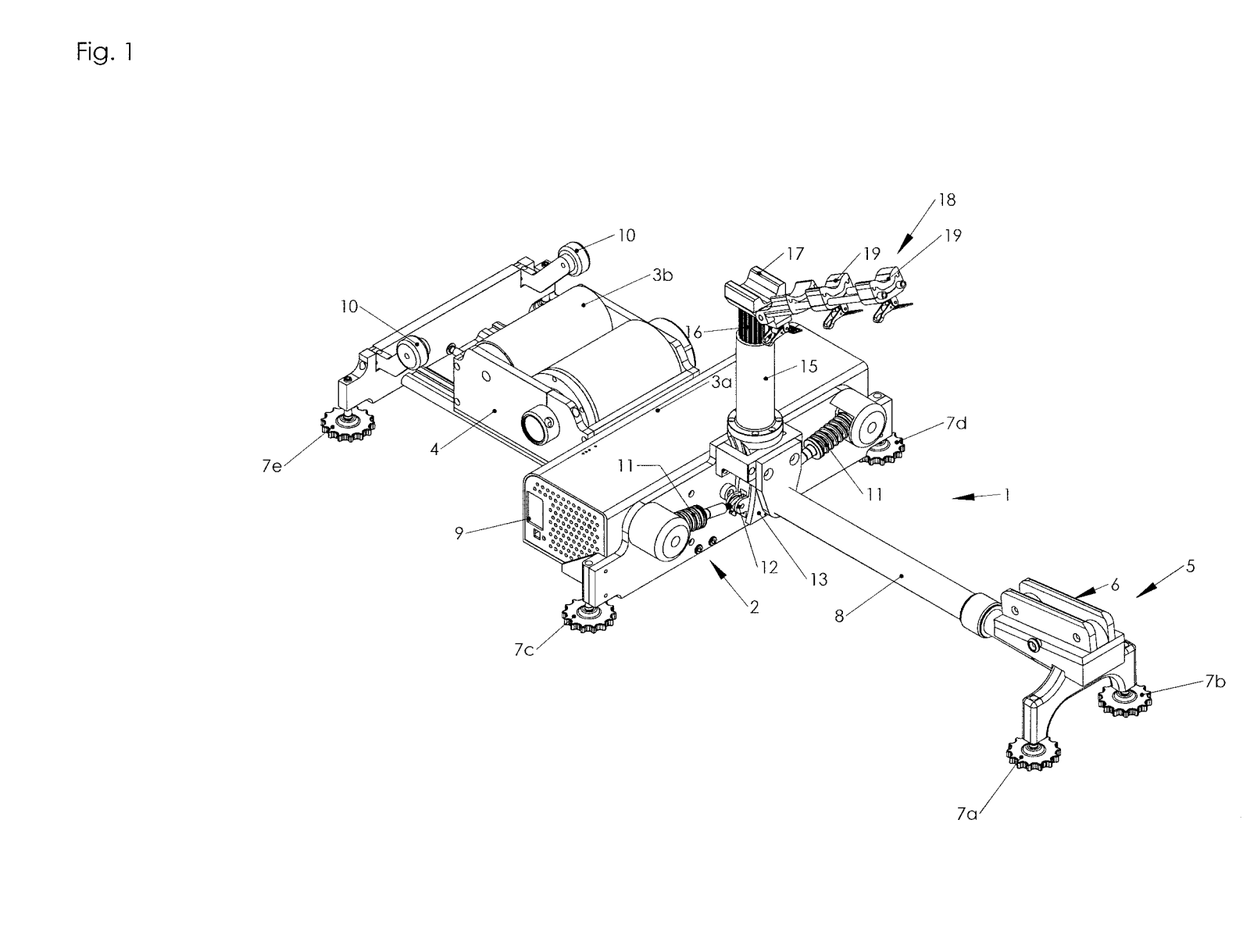
FIGS. 1 and 2 perspective views of a preferred embodiment of the bicycle trainer according to the present invention.
Figure 2:
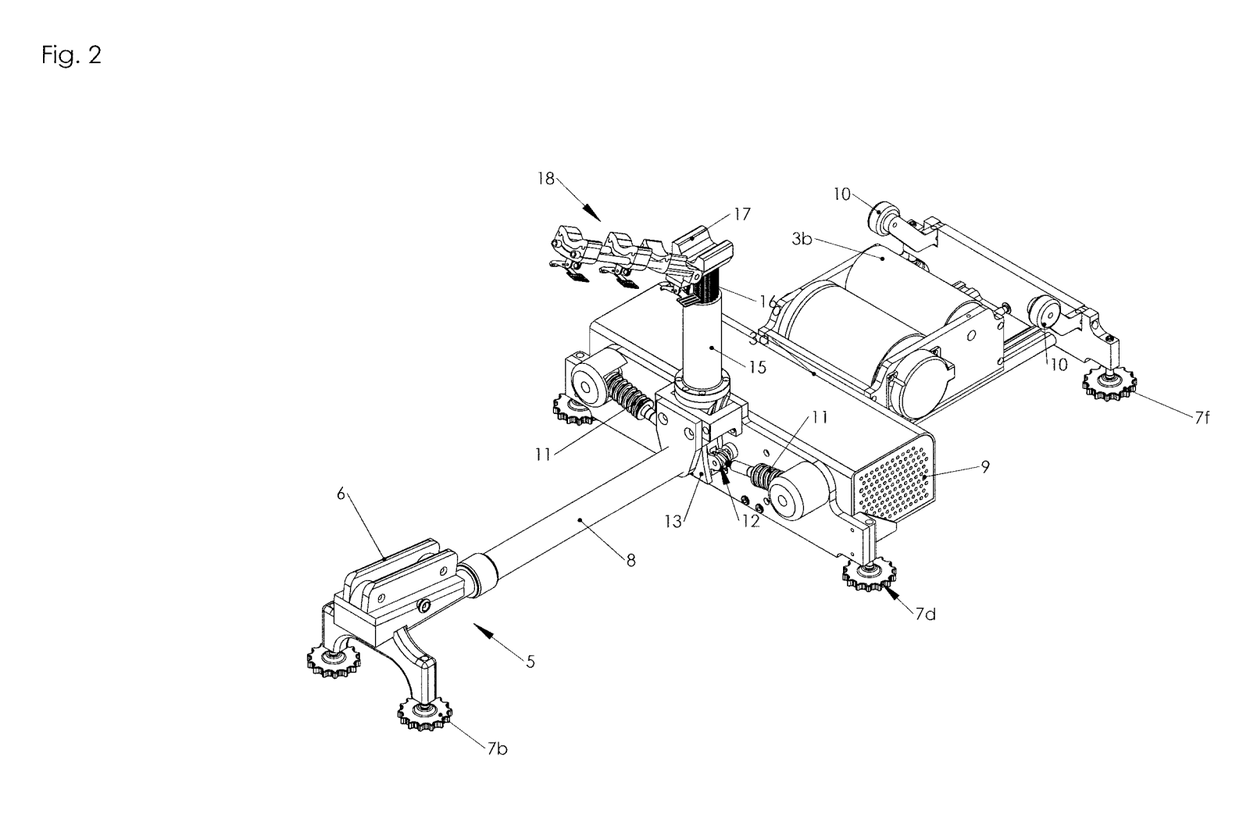
Figure 3:
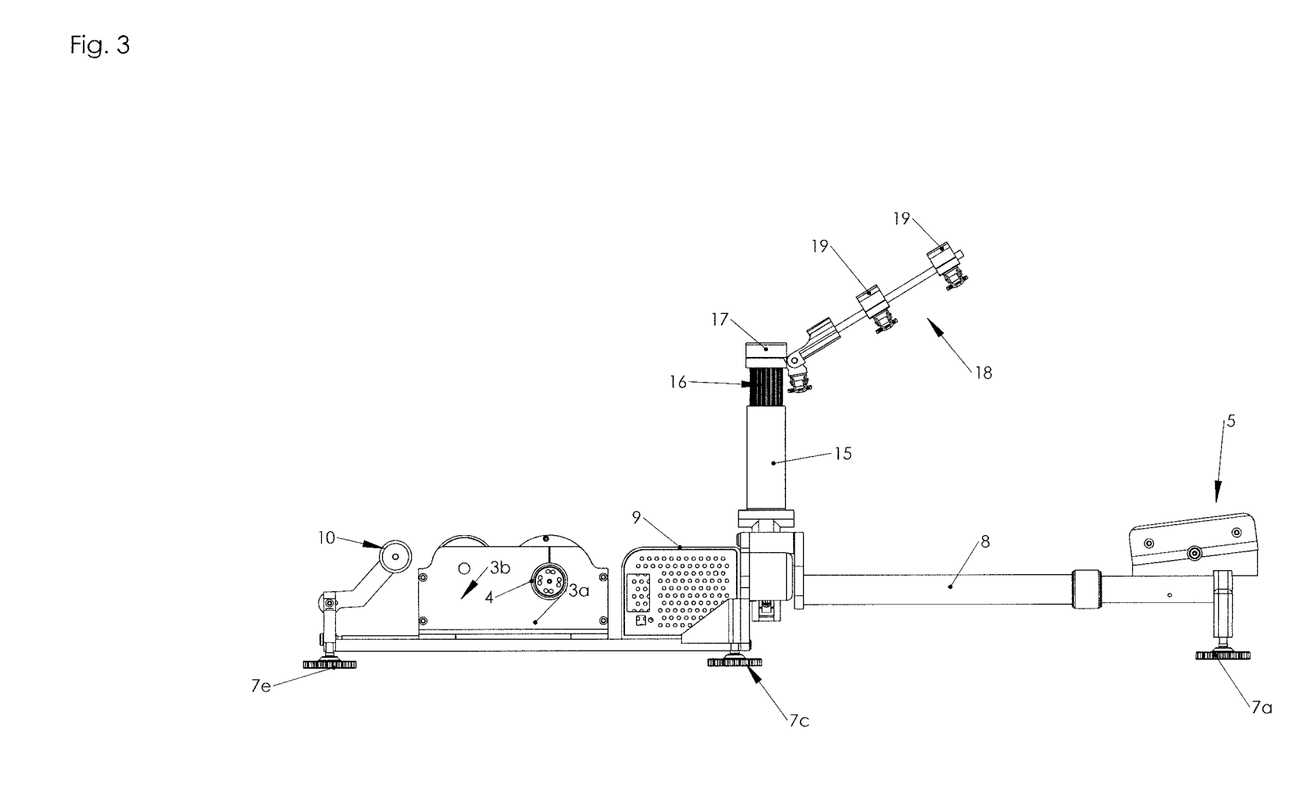
FIGS. 3 and 4 side views of the preferred embodiment of the bicycle trainer according to the present invention.
Figure 4:
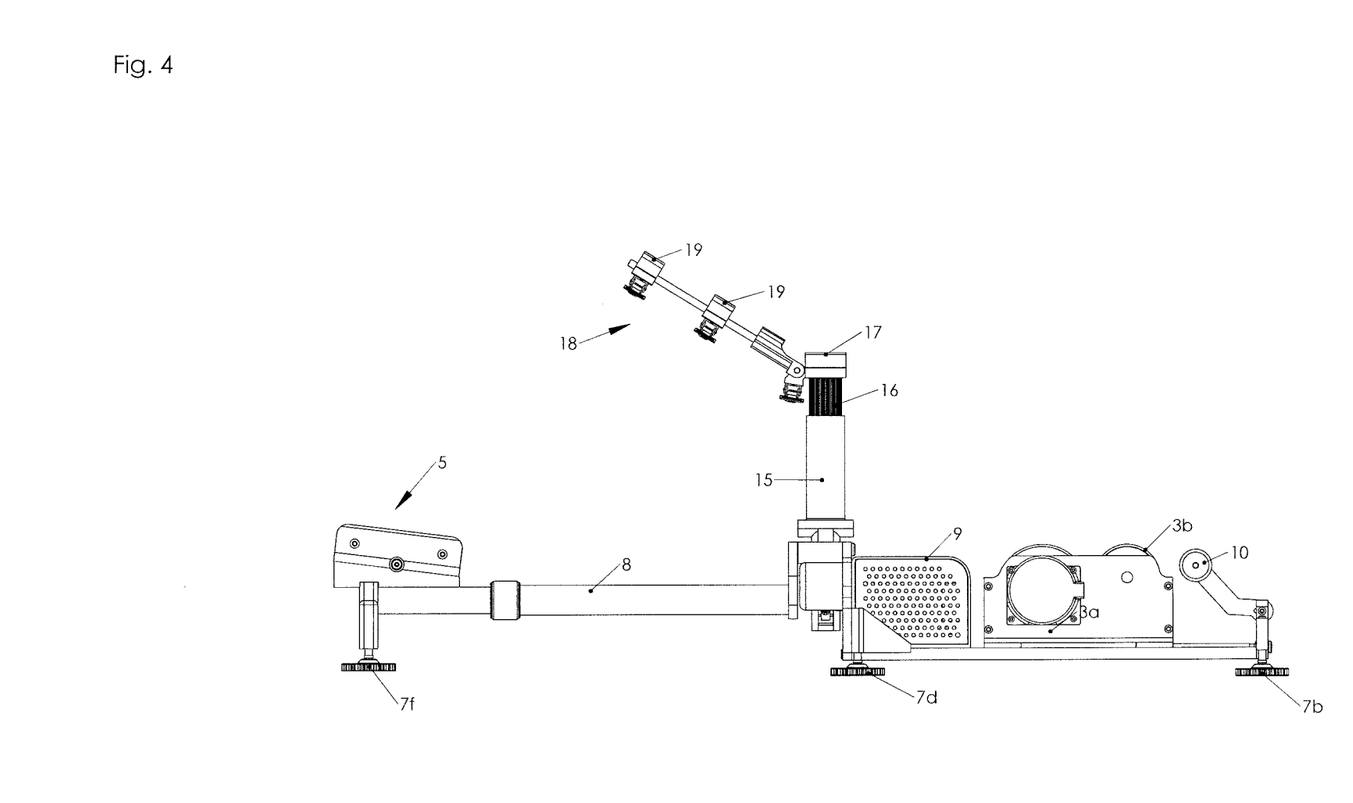
Figure 5:
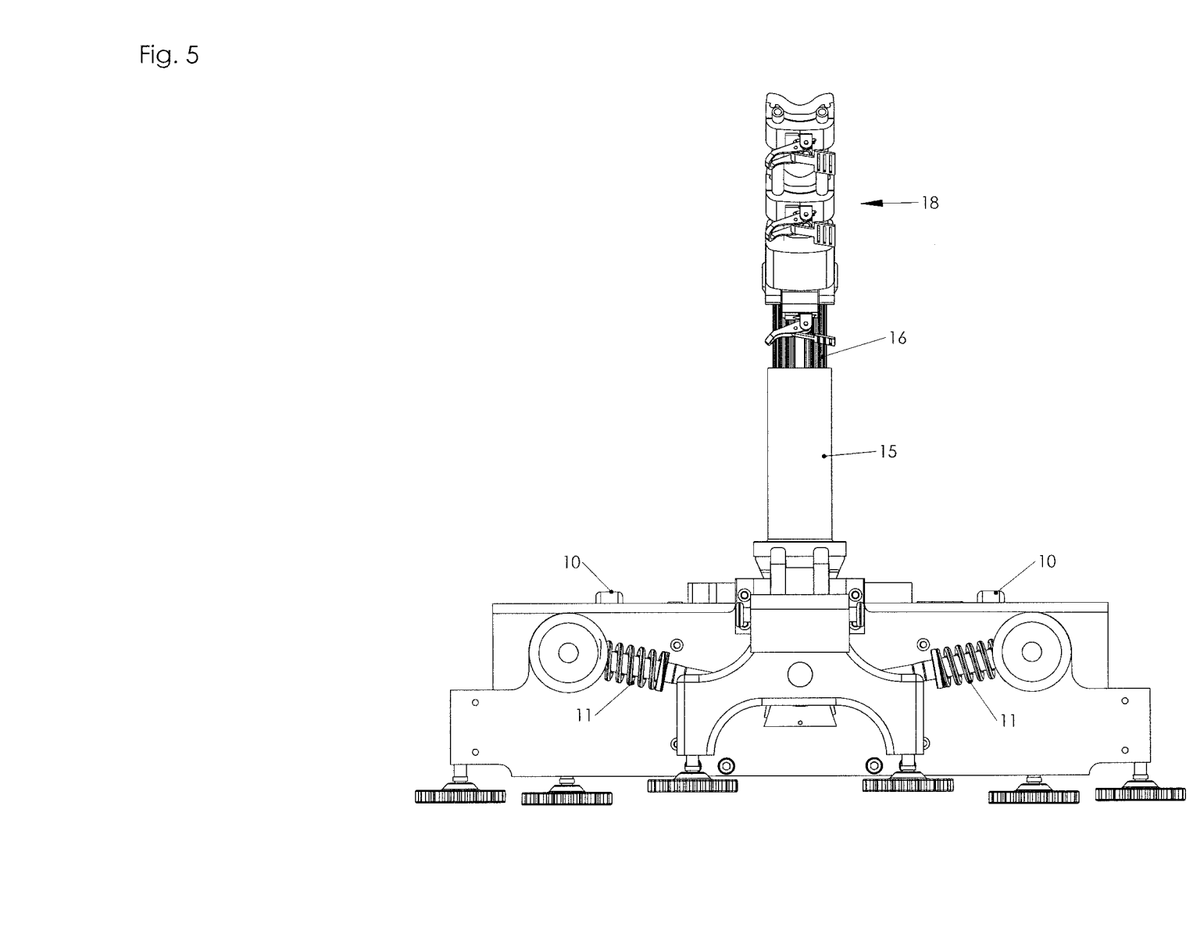
FIG. 5 a front view of the preferred embodiment of the bicycle trainer according to the present invention.
Figure 6:
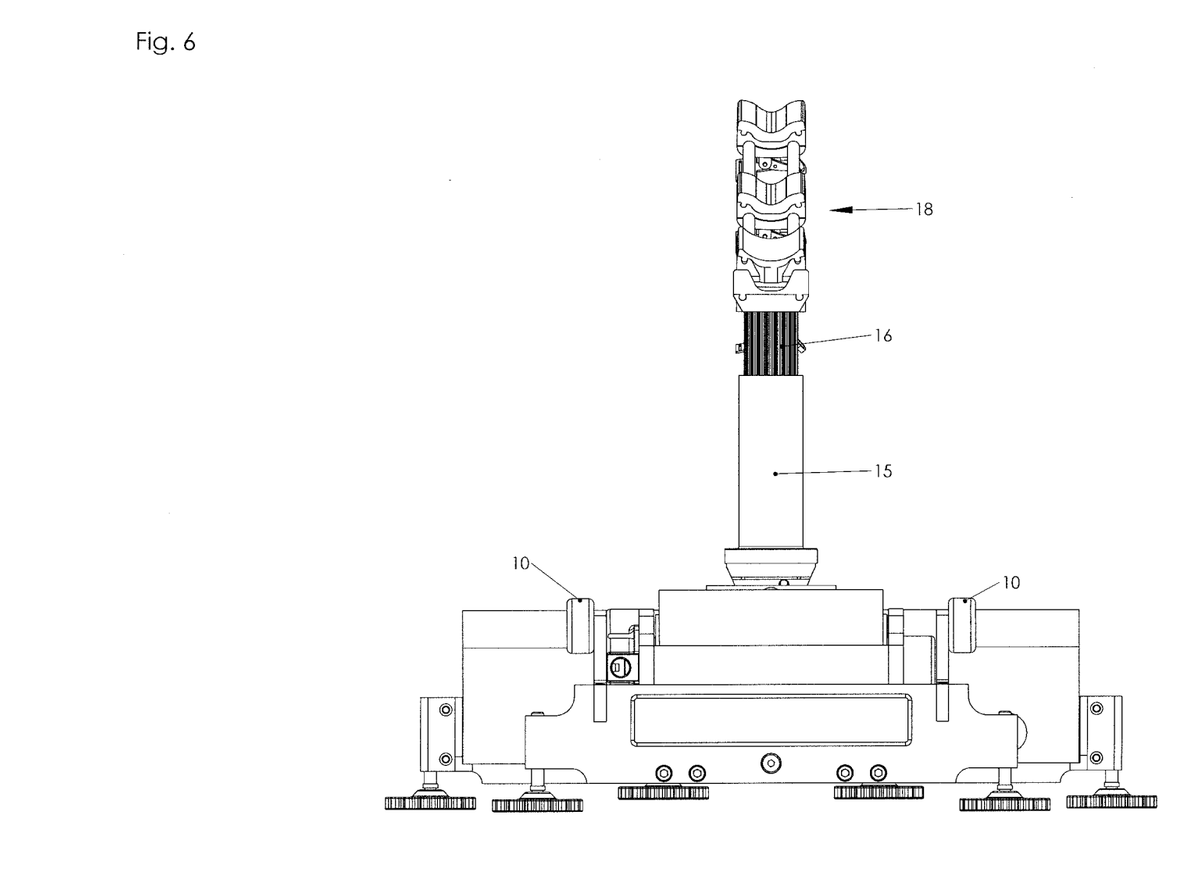
FIG. 6 a rear view of the preferred embodiment of the bicycle trainer according to the present invention.
Figure 7:
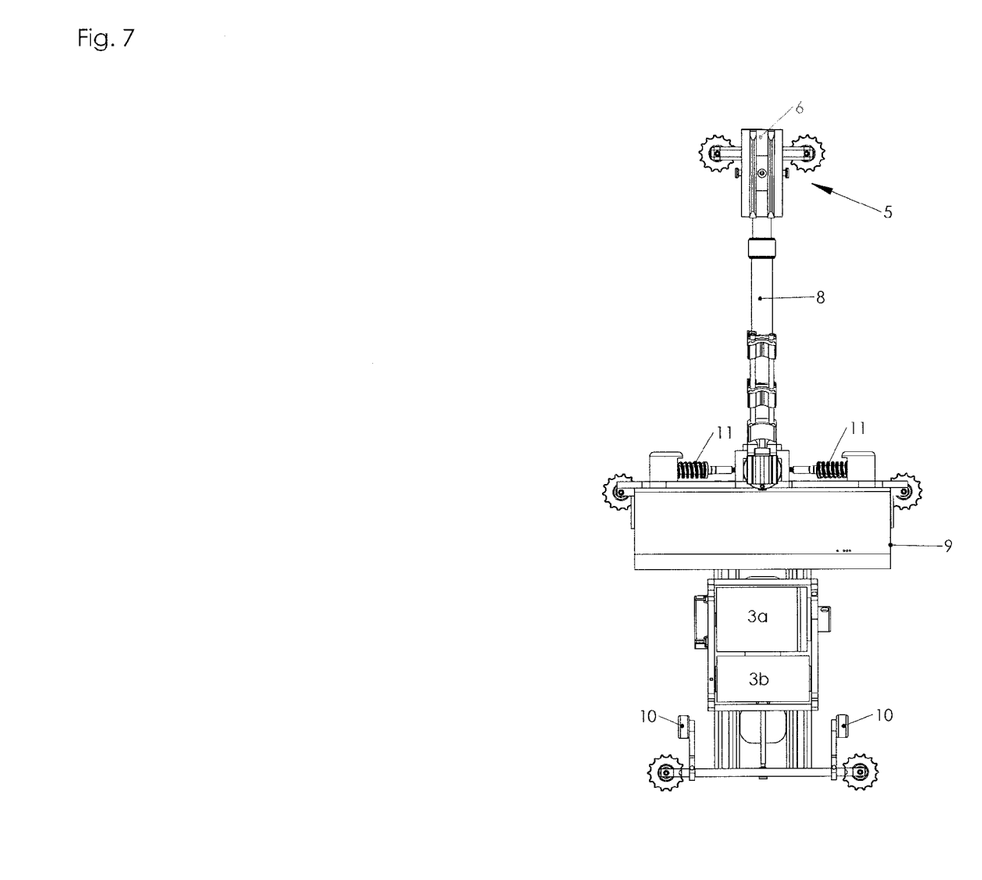
FIG. 7 a top view of the preferred embodiment of the bicycle trainer according to the present invention.
Figure 8:
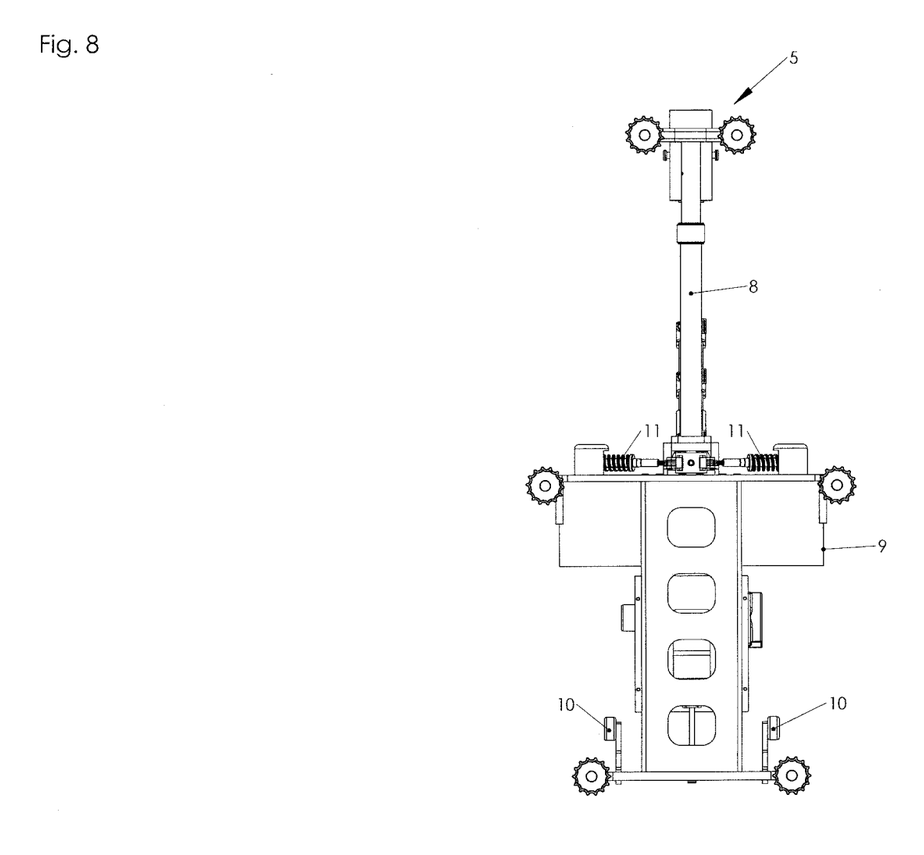
FIG. 8 a bottom view of the preferred embodiment of the bicycle trainer according to the present invention.

FIGS. 1 to 8 show the preferred embodiment in perspective view (FIGS. 1 and 2), in a side view (FIGS. 3 and 4), in a front view (FIG. 5), in a back view (FIG. 6), in a top view (FIG. 7) and in a bottom view (FIG. 8). The bicycle trainer according to this preferred embodiment comprises a support 1 for supporting a bicycle (not shown) having a frame and a rear wheel attached to a rear axle. The support 1 comprises means 2 for biasing the bicycle into an upright orientation. The bicycle trainer further comprises a roller 3a for engaging with the rear wheel of the bicycle. When the bicycle is supported by the support 1, the roller is adapted to provide resistance against turning the rear wheel. The rear axle of the bicycle is not connected to the support 1. The rear wheel of the bicycle rests, during use, on the roller 3a as well as on the second roller 3b. Because the roller 3a is connected to the support, the rear axle of the bicycle is arguably indirectly connected to the support via the rear wheel and the roller 3a. However, the present invention is understood in such a manner that the roller 3a is not part of the support 1 (even though connected thereto) and that the resting of the rear wheel on the roller 3a is not to be understood as a connection between the rear axle and the support. In particular, the rear axle of the bicycle is not mounted to the support in any way.

Rather, the rear wheel rests freely on, and is supported by, the first roller 3a and the second roller 3b. The front wheel of the bicycle rests on, and is supported by, a mounting portion 5 which preferably comprises means 6 for engaging the tire of the front wheel. The width of the slot for receiving the tire of the front wheel of the means 6 is preferably adjustable. Even though not required, the front wheel may in addition be fixed to the mounting portion 5 by means of an additional fixation element such as a rope or a strap. The distance between the mounting portion 5 for the front wheel and the two rollers 3a and 3b is preferably adjustable by the cylinder and piston 8. Thus, the bicycle trainer of the present invention can be adapted to any type and size of bicycle.

The mounting of the bicycle to the support 1 is achieved via the means 2 for biasing the bicycle into an upright orientation. The means 2 comprises a system of posts and rods. Inter alia, the means comprises a cylinder 15 and a piston 16 which can move up and down within the cylinder 15. Preferably, the outer surface of the piston has a grooved or riffled surface which engages with an accordingly grooved or riffled inner surface of the cylinder 15 in order to avoid rotation of the piston 16 within the cylinder 15. A means 17 for receiving and supporting a portion of the frame of the bicycle is preferably provided on top of the piston 16. In addition, the system of posts and rods comprises a bar 18 or the like for mounting the down tube of the bicycle to the means for biasing the bicycle into an upright orientation. In the preferred embodiment, the bar 18 comprises two rods and two adapters 19, which can slidably move along these two rods. These adapters 19 are adapted to engage with and to be mounted to the down tube of the bicycle frame. The adapters 19 may comprise any known releasable fastening system. Preferably, the adapters comprise straps for winding around the down tube of the bicycle frame which may then be tightened and fastened.

The bar 18 is preferably pivotably attached to the piston 16 in order to be adjustable to different orientations of the down tube of the bicycle frame. Once mounted, the bicycle frame rests on the means 17 and is attached to the two adapters 19. However, the dimensions of the piston 16 and the cylinder 15 are preferably chosen in such a manner that the bicycle, once mounted, rests on the rollers 3a and 3b on the one hand and on the mounting portion 5 for the front wheel on the other hand. Yet, no substantial vertical upright force is transmitted from the means for biasing the bicycle into an upright orientation as long as the bicycle is oriented vertically. Moreover, since the piston 16 may move freely up and down within the cylinder 15, the entire bicycle can, once mounted, be lifted off the support.

The entire means for biasing the bicycle into an upright orientation is adapted to allow for a tilting movement of the bicycle. For this purpose, the cylinder 15 can be rotated or pivoted about a longitudinal axis (parallel to the piston and cylinder 8). However, pivoting the cylinder 15 compresses either of the two springs 11 which are connected via a mounting 12 to the cylinder 15, respectively. Preferably, the springs 11 have play in one direction. Accordingly, pivoting the cylinder 15 compresses one of the two springs 11, whereas the other of the two springs 11 is not expanded by force. The mounting portions 12 can preferably be moved upwards and downwards along the segment of a circle 13. Moving the mounting portions 12 along said circle segment does not change the compression of the springs 11, yet reduces or increases the lever arm acting from the cylinder 15 onto the springs 11. Preferably, the mounting portions 12 can be moved upwards and downwards by means of a motor and a spindle within the cylinder 15.

If a bicycle is mounted to the bicycle trainer and the user on the bicycle leans towards one side, the bicycle together with the cylinder 15 tilts away from the vertical and thereby compresses one of the springs 11. In response, this compressed spring 11 provides a torque biasing the bicycle back into an upright orientation. The amount of said torque can be adjusted by moving the mounting portions 12 upwards and downwards as discussed above. Thus, the user is provided with a certain amount of freedom to move on the bicycle, yet stabilized by the biasing torque. Preferably, a stop is provided which avoids a tilting movement of the cylinder 15 (and the bicycle, accordingly) beyond a predetermined critical angle versus the vertical.

Once mounted, the user may pedal on the bike in order to turn the rear wheel. The roller 3a, which is driven by a motor 4 being provided within the roller 3a actively provides resistance against turning the rear wheel and preferably also actively accelerates the rear wheel if needed. The second roller 3b can preferably freely rotate. The motor 4 within the roller 3a as well as the additional motor for adjusting the torque can be controlled by the controller unit 9. The controller unit or processor 9 can preferably be connected to a display and/or a computer in order to allow for displaying a certain training profile and/or for predefining specific parameters of a specific training unit.

The entire bicycle trainer rests on six feet 7a to 7f which are adjustable in height. Moreover, the bicycle trainer preferably comprises two additional rollers or wheels 10 which may be pivoted out of their resting position as shown in the Figures to allow for an easy movement of the bicycle trainer.

The invention claimed is:
1. A bicycle trainer for mounting a bicycle having a frame and a rear wheel attached to a rear axle, the bicycle trainer comprising:
two rollers adapted to engage with the rear wheel of the bicycle, one of the two rollers being adapted to transmit a driving force and a braking force to the rear wheel,
a motor adapted to actively provide the driving and braking forces to said one of the two rollers, and
an electronics unit adapted to control the motor, a support configured to mount a front wheel of the bicycle thereon, wherein the bicycle trainer is so configured that the slope of a line connecting said one of the two rollers to the support configured to mount the front wheel thereon is adjustable;

wherein, when the bicycle is mounted to the trainer, the bicycle is, at least in part, supported by the two rollers, and wherein the support comprises a platform configured to tilt to effect said adjustment of slope.

2. The bicycle trainer according to claim 1, wherein the electronics unit is adapted to simulate driving and braking forces of a predetermined track within a predetermined terrain.

3. The bicycle trainer according to claim 2, wherein the predetermined terrain comprises at least one of slope and rolling resistance.

4. The bicycle trainer according to claim 2, wherein the simulation of the driving and braking forces takes the weight of a user into account.

5. The bicycle trainer according to claim 1, wherein the electronics unit is adapted to simulate driving and braking forces under predetermined environmental conditions.

6. The bicycle trainer according to claim 5, wherein the predetermined environmental conditions comprise at least one of wind, rain, humidity, temperature and rider's inertia.

7. The bicycle trainer according to claim 1, wherein the electronics unit is adapted to measure the force transmitted from the rear wheel to the roller.

8. The bicycle trainer according to claim 7, wherein the driving and braking forces provided to said one of the two rollers are adjusted in response to the measured force.

9. The bicycle trainer according to claim 1, wherein the electronics unit is adapted to provide data for displaying terrain data and/or environmental conditions.

10. The bicycle trainer according to claim 9, wherein the electronics unit is adapted to save and/or upload track data of a user of the trainer and/or a professional cyclist and to provide comparative data for displaying which allow for a direct comparison of the current performance of the user with the saved and/or uploaded track data.

11. The bicycle trainer according to claim 10, wherein the track data comprises at least one of the following data: velocity, revolution speed, and heart rate.

12. The bicycle trainer according to claim 9, wherein the electronics unit is adapted to receive a live track data stream and to provide comparative data for displaying which allow for a direct comparison of the current performance of a user of the trainer with a simultaneous performance evaluated from the live track data stream.

13. The bicycle trainer according to claim 1, wherein, when the bicycle is mounted to the trainer, at least 10% of the weight of the bicycle is supported by the roller.

14. The bicycle trainer according to claim 1, further comprising a motor adapted to vibrate the platform.

15. A method for comparative home training comprising the following steps:
a) providing a bicycle trainer comprising two rollers configured to engage with a rear wheel of a bicycle, one of the two rollers being adapted to transmit a driving force and a braking force to the rear wheel, a motor adapted to actively provide driving and braking forces to said one of the two rollers, an electronics unit adapted to control the motor, and a support configured to mount a front wheel of the bicycle thereon, wherein the bicycle trainer is so configured that the slope of a line connecting said one of the two rollers to the support configured to mount the front wheel thereon is adjustable, wherein the support comprises a platform configured to tilt to effect said adjustment of slope;
b) mounting a bicycle having a frame, a rear wheel and a front wheel onto the bicycle trainer such that the rollers engage with the rear wheel of the bicycle and the front wheel of the bicycle is mounted on the support;
c) providing a display;
d) uploading data of a predetermined track onto the electronics unit;
e) simulating the predetermined track by actively providing driving and braking forces to said one of the two rollers and by displaying at least some of the data while a user is cycling on the bicycle.

16. The method according to claim 15, wherein the data comprises terrain data.

17. The method according to claim 16, wherein the predetermined terrain comprises at least one of slope and rolling resistance.

18. The method according to claim 15, wherein the data comprises environmental conditions.

19. The method according to claim 18, wherein the predetermined environmental conditions comprise at least one of wind, rain, humidity, temperature and rider's inertia.

20. The method according to claim 15, wherein the data comprises image data along the predetermined track.

21. The method according to claim 15, wherein the simulating of the predetermined track comprises calculating the driving and braking forces on a basis of at least one of: slope, rolling resistance, wind, rain, humidity, temperature, inertia, weight of the user.

22. The method according to claim 15, further comprising measuring the force transmitted from the rear wheel to said one of the rollers.

23. The method according to claim 22, wherein the simulating of the predetermined track comprises adjusting the driving and braking forces provided to the roller in response to the measured force.

24. The method according to claim 15, wherein simulating the predetermined track comprises displaying image data along the predetermined track.

25. The method according to claim 15, further comprising uploading track data of a user of the trainer and/or a professional cyclist and displaying comparative data which allow for a direct comparison of the current performance of the user with the saved and/or uploaded track data.

26. The method according to claim 25, wherein the track data comprises one or a combination of the following data: velocity, revolution speed, and heart rate.

27. The method according to claim 15, further comprising uploading a live track data stream of a user of the trainer and/or a professional cyclist and displaying comparative data which allow for a direct comparison of the current performance of the user with a simultaneous performance evaluated from the live track data stream.

28. The method according to claim 25, further comprising measuring and/or calculating at least one of the following data of the user's performance: velocity, revolution speed, and heart rate.

* * * * *